United States Patent [19]

Ide et al.

[11] 4,176,132
[45] Nov. 27, 1979

[54] REACTION OF ORGANIC DIISOCYANATES WITH WATER

[75] Inventors: Akira Ide; Sojiro Matsumoto, both of Nobeoka, Japan

[73] Assignee: Asahi Kasei Kogyo Kabushiki Kaisha, Osaka, Japan

[21] Appl. No.: 882,466

[22] Filed: Mar. 1, 1978

[30] Foreign Application Priority Data

Mar. 1, 1977 [JP] Japan .................................. 52-21882
Jan. 20, 1978 [JP] Japan .................................. 53-5053
Feb. 6, 1978 [JP] Japan .................................. 53-12097

[51] Int. Cl.$^2$ .............. C07C 119/042; C07C 119/045; C07C 119/048
[52] U.S. Cl. .................... 260/453 A; 260/453 AB; 260/453 AL; 260/453 AR; 260/453 SP
[58] Field of Search .... 260/453 A, 453 AL, 453 AR, 260/453 AB

[56] References Cited

U.S. PATENT DOCUMENTS

| | | | |
|---|---|---|---|
| 2,885,420 | 5/1959 | Spiegler | 260/453 SP |
| 3,896,154 | 7/1975 | Takahashi et al. | 260/453 P |
| 3,903,127 | 9/1975 | Wagner et al. | 260/453 AB |
| 4,028,392 | 6/1977 | Ogawa et al. | 260/453 AR |
| 4,072,702 | 2/1978 | Auskins | 260/453 AB |

*Primary Examiner*—Dolph M. Torrence

*Attorney, Agent, or Firm*—Sughrue, Rothwell, Mion, Zinn and Macpeak

[57] ABSTRACT

A process for producing an organic polyisocyanate having a long storage life which comprises reacting an aliphatic, alicyclic or araliphatic diisocyanate monomer with water in the presence of a solvent comprising a mixture of at least one ethylene glycol derivative represented by the formula (I):

$$R_1O(CH_2CH_2O)_nR_2 \qquad (I)$$

wherein $R_1$ and $R_2$, which may be the same or different, each represents an alkyl group having 1 to 4 carbon atoms, which may be straight chain or branched chain, or an acetyl group and n is an integer of 1 to 2; and at least one phosphoric acid derivative represented by the formula (II):

$$\begin{array}{c} R_3O \\ R_4O-P=O \\ R_5O \end{array}$$

wherein $R_3$, $R_4$ and $R_5$, which may be the same or different, each represents a methyl group or an ethyl group.

22 Claims, No Drawings

REACTION OF ORGANIC DIISOCYANATES WITH WATER

BACKGROUND OF THE INVENTION

1. Field of the Invention

This invention relates to a process for producing an organic polyisocyanate having a long storage life, and more particularly, to a process for producing an organic polyisocyanate having a long storage life which comprises reacting an aliphatic, alicyclic or araliphatic diisocyanate monomer with water in the presence of a specific solvent mixture.

2. Description of the Prior Art

Because of the presence of an isocyanate group which is reactive with an active hydrogen, organic polyisocyanates obtained by reacting an organic diisocyanate monomer with water find utility in preparing foaming agents, paints and adhesives. Of these applications, use of organic polyisocyanates as an ingredient of a paint is increasingly gaining acceptance because organic polyisocyanates provide a paint film with good physical properties.

A film of a paint prepared from aromatic polyisocyanates yellows, cracks or peels a few months after painting, whereas a film of a paint prepared from aliphatic, alicyclic or araliphatic polyisocyanates retains its initial physical properties for a few years without deterioration. Although aliphatic, alicyclic or araliphatic polyisocyanates have good physical properties, they also have inherent disadvantages. For example, reaction between an organic diisocyanate monomer and water inevitably produces polyurea as a precipitate (as disclosed in U.S. Pat. No. 3,124,605, U.S. Pat. No. 3,903,127, Japanese Patent Publication No. 16448/62, and Japanese Patent Application (OPI) No. 134629/74). According to the processes disclosed in these prior art references, a transient emulsion is formed due to the low miscibility of an organic diisocyanate monomer and water. The reaction between the diisocyanate monomer and water which is slightly dissolved in the diisocyanate monomer phase produces the desired polyisocyanate, but if water reacts with the diisocyante monomer slightly dissolved in the water phase, polyurea is precipitated as a by-product. Precipitation of polyurea is not only uneconomical but it reduces the commercial value of the polyisocyanate end-product.

The amount of by-product polyurea produced varies depending upon temperature, stirring rate, ratio of diisocyanate monomer to water, etc., but the amount is generally 0.5 wt% or more based on the weight of the polyisocyanate end-product. The production of polyurea as a by-product can be minimized by addition of 40 mol or more of diisocyanate monomer per mol of water, but it is impossible to completely prevent the production of polyurea as a by-product. Moreover, when this proportion of diisocyanate monomer to water is used, the large excess of diisocyanate monomer must be removed from the polyisocyanate, and this results in a complex manufacturing procedure, which is uneconomical.

U.S. Pat. No. 4,028,392 discloses an isocyanate prepolymer of a specific formula and a process for producing such. This process described in U.S. Pat. No. 4,028,392, comprises reacting a diisocyanate monomer with water in the presence of a hydrophilic organic solvent such as a carboxylic acid ester, a phosphoric acid ester, an amide, a ketone, a nitrile, an ether and the like. However, the disclosure set forth in U.S. Pat. No. 4,028,392 does not teach or suggest the use of the unique solvent mixture employed in this invention nor the advantageous results which are obtained when such a mixture is used over the use of the solvents individually, as demonstrated in Reference Examples 1–6 given hereinafter.

A further disadvantage with polyisocyantes produced using prior art processes is that the monomer content in the polyisocyanate increases on storage for a long period. This poses a serious problem in spray painting because any diisocyanate monomer contained in the mist of the paint can cause pollution problems, and can have an adverse effect on the human body as well as the painted object. Therefore, it is desired to minimize the diisocyanate monomer content in the polyisocyanate.

Commercially available polyisocyanates contain 1 to 2 wt% diisocyanate monomer and have a very high viscosity of about 6,000 to 10,000 cP at 30° C., so that they must be diluted with a suitable solvent before use, and this has been another cause of pollution problems. It is therefore desired to be able to produce a high-solid type paint or a solventless paint using polyisocyanates of low viscosity. A polyisocyanate with a low viscosity can be prepared by increasing the molar ratio of the diisocyanate monomer to the water, but unfortunately this results in a further increase in the monomer content in the resulting polyisocyanate on storage for a long period of time.

SUMMARY OF THE INVENTION

As a result of various studies on a process that is free from the defects of conventional methods of producing organic polyisocyanates, it has now been found that such defects can be eliminated by reacting an organic diisocyanate monomer and water in the presence of a solvent comprising a mixture of an ethylene glycol derivative and a phosphoric acid derivative.

According to the process of this invention, an organic polyisocynanate having a long storage life can be produced without formation of polyurea as a by-product by reacting an aliphatic, alicyclic or araliphatic diisocyanate monomer with water and conducting the reaction (a) at a reaction temperature of at least about 70° C.;

(b) in the presence of a solvent mixture comprising a mixture of at least one ethylene glycol derivative of the formula (I):

$$R_1O(CH_2CH_2O)_nR \qquad (I)$$

wherein $R_1$ and $R_2$, which may be the same or different, each represents an alkyl group having 1 to 4 carbon atoms, which may be straight chain or branched chain, or an acetyl group and n is an integer of 1 to 2; and at least one phosphoric acid derivative of the formula (II):

$$\begin{aligned}R_3O\!\!&\diagdown\\ R_4O\!\!&-\!\!P\!=\!O\\ R_5O\!\!&\diagup\end{aligned} \qquad (II)$$

wherein $R_3$, $R_4$ and $R_5$, which may be the same or different, each represents a methyl gorup or an ethyl group;

(c) with the proportion of the solvent mixture in the reaction mixture being 10 to 80 wt%; and (d) with the proportion of the ethylene glycol derivative (I) in the solvent mixture being 30 to 90 wt% and the proportion of the phosphoric acid derivative (II) in the solvent mixture being 10 to 70 wt%.

DETAILED DESCRIPTION OF THE INVENTION

From the standpoint of the economical recovery of solvent, the phosphoric acid derivative used as one of the two components of the solvent mixture employed in this invention is very advantageous because only a minimum amount of the phosphoric acid derivative is required for dissolving water. The phosphoric acid derivative provides a homogeneous phase of diisocyanate monomer and water throughout the process of the reaction, thus completely inhibiting the formation of the by-product polyurea. When the phosphoric acid derivative is used alone as a solvent, however, a significant amount of the monomer is liberated by the polyisocyanate obtained on storage for a long period. This defect can first be eliminated by using the phosphoric acid derivative of the formula (II) with an ethylene glycol derivative of the formula (I), where the ethylene glycol derivative cannot completely prevent the formation of polyurea on its own. It is extremely difficult to filter out the polyurea produced as a by-product, and the polyurea tends to clog the filter upon filtration. Further, when a filter having low filtration resistance is used, the polyurea passes through the filter so that the quality of the desired product (i.e., polyisocyanate) is degraded. As a matter of course, when continuous filteration is carried out, clogging of the filter prevents continuous processings. Therefore, it is highly desirable for the production of polyurea to be avoided.

Therefore, in the process of this invention a solvent comprising a mixture of an ethylene glycol derivative of the formula (I) and a phosphoric acid derivative of the formula (II) must be used so as to prevent the formation of polyurea and liberation of the monomer on storage.

According to the process of this invention, a stable polyisocyanate product from which only a small amount of the monomer is liberated during long storage is obtained. In addition, by selecting suitable reaction conditions, a good material for a paint and having a narrow molecular-weight distribution, a low molecular weight, a low viscosity and high isocyanate content is obtained.

Suitable organic diisocyanate monomers which can be used in the process of this invention are aliphatic, alicyclic or araliphatic diisocyanate monomers other than those having an isocyanate group directly bonded to an aromatic ring. Suitable examples of these diisocyanate monomers include ethylene diisocyanate, tetramethylene diisocyanate, hexamethylene diisocyanate, lysine diisocynate, isophorone diisocyanate, xylylene diisocyanate, cyclohexane-1,4-diisocyanate, etc. These organic diisocyanate monomers can be used individually or as a mixture thereof.

The ethylene glycol derivatives of the formula (I) above which are used in the process of this invention should be chemically stable and should not react with an isocyanate group of the diisocyanate monomer or with the phosphoric acid derivative of the formula (II), should be freely mixed with the phosphoric acid derivative of the formula (II) and should dissolve both the diisocyanate monomer and water to provide a homogeneous reaction system. The ethylene glycol drivatives are used in this invention in an amount necessary and sufficient to provide such a homogenous system.

Of the ethylene glycol derivatives of the formula (I) which can be used in this invention, ethylene glycol derivatives capable of dissolving more than about 0.5% water are preferred since the lower the solubility of water in the ethylene glycol derivative of the formula (I) is, the larger is the amount of the ethylene glycol derivative of the formula (I) needed and this results in the necessity of separation and recovery of the solvent after the reaction which is uneconomical. In addition, in order to subsequently recover the solvent economically, ethylene glycol derivatives of the formula (I) having a boiling point not much lower than that of water and lower than that of polyisocyanate are preferred. A suitable boiling point ranges from about 120° C. to 300° C.

Examples of suitable ethylene glycol derivatives of the formula (I) that satisfy these requirements are ethylene glycol monomethyl ether acetate, ethylene glycol monoethyl ether acetate, ethylene glycol mono-n-propyl ether acetate, ethylene glycol mono-isopropyl ether acetate, ethylene glycol mono-n-butyl ether acetate, ethylene glycol diacetate, ethylene glycol dimethyl ether, ethylene glycol diethyl ether, ethylene glycol di-n-propyl ether, ethylene glycol diisopropyl ether, ethylene glycol di-n-butyl ether, ethylene glycol methyl ethyl ether, ethylene glycol methyl-n-propyl ether, ethylene glycol methyl isopropyl ether, ethylene glycol methyl n-butyl ether, ethylene glycol ethyl n-propyl ether, ethylene glycol ethyl isopropyl ether, ethylene glycol ethyl n-butyl ether, ethylene glycol isopropyl n-butyl ether, ethylene glycol n-propyl n-butyl ether, diethylene glycol monomethyl ether acetate, diethylene glycol monoethyl ether acetate, diethylene glycol monoisopropyl ether acetate, diethylene glycol mono-n-propyl ether acetate, diethylene glycol mono-n-butyl ether acetate, diethylene glycol diacetate, diethylene glycol dimethyl ether, diethylene glycol diethyl ether, diethylene glycol diisopropyl ether, diethylene glycol di-n-propyl ether, diethylene glycol di-n-butyl ether, diethylene glycol methyl ethyl ether, diethylene glycol methyl isopropyl ether, diethylene glycol methyl n-propyl ether, diethylene glycol methyl n-butyl ether, diethylene glycol ethyl isopropyl ether, diethylene glycol ethyl n-propyl ether, diethylene glycol ethyl n-butyl ether, diethylene glycol propyl n-butyl ether. These ethylene glycol derivatives of the formula (I) may be used individually or as a mixture thereof.

Of those ethylene glycol derivatives of the formula (I) above, ethylene glycol derivatives in which $R_1$ and $R_2$ is an alkyl group having 1 to 2 carbon atoms or an acetyl group are preferred, and further ethylene glycol monomethyl ether acetate, diethylene glycol dimethyl ether, ethylene glycol monoethyl ether acetate and ethylene glycol diacetate are particularly preferred. Ethylene glycol derivatives in which $R_1$ and/or $R_2$ in the formula (I) is an alkyl group with 5 or more carbon atoms have poor solubility of water, and when these are used as one of the two components of the solvent mixture, polyurea is produced as a by-product. These ethylene glycol derivatives are also disadvantageous in that a separation of the monomer, which is undesirable, can not be prevented when the resulting polyisocyanate is stored for a long period of time.

The phosphoric acid derivative of the formula (II) above which can be used in the present invention must be chemically stable, must not be reactive with an isocyanate group and must be capable of dissolving the ethylene glycol derivative of the formula (I) above, the diisocyanate monomer, the reaction product and water with a homogeneous reaction system being produced. Those phosphoric acid derivatives of the formula (I) which can be freely mixed with water are particularly preferred. The phosphoric acid derivative of the formula (II) preferably has a boiling point significantly above that of water, and more specifically from about 180° C. to about 310° C., and to achieve an economical recovery of such in a subsequent step, the boiling point of the phosphoric acid derivative of the formula (I) is preferably lower than that of the polyisocyanate ultimately obtained.

Examples of suitable phosphoric acid derivatives of the formula (II) that meet these requirements are trimethyl phosphate triethyl phosphate, dimethyl ethyl phosphate and diethyl methyl phosphate. These can be used individually or they may be mixed together at any proportions. Further, tripropyl phosphate, tributyl phosphate can be used in combination with trimethyl phosphate, triethyl phosphate or a mixture thereof although tripropyl phosphate and tributyl phosphate are not preferred for use alone since these phosphates have less solubility in water than that of trimethyl phosphate or triethyl phosphate, and cause polyurea to precipitate during the reaction.

The amount of the solvent mixture to be used in the process of this invention will vary depending upon the proportion of the phosphoric acid derivative of the formula (II) to the ethylene glycol derivative of the formula (I) and the solubility of water in the individual solvents, but, in general, the amount of the solvent mixture will range from 10 to 80% by weight, preferably from 20 to 50% by weight, based on the total weight of the reaction mixture. If the solvent mixture is used in an amount less than 10% by weight, water is not dissolved sufficiently by the solvent mixture so that a homogeneous reaction system is not obtained, whereas the use of more than 80% by weight of the solvent mixture is uneconomical because the amount of the solvent mixture to be recovered is increased. The composition of the solvent mixture should be decided such that the effects of the individual solvents are maximized, and thus the proportion of the ethylene glycol derivative of the formula (I) ranges from 30 to 90% by weight, preferably 50 to 70% by weight, based on total amount of the solvent mixture. If the amount of the ethylene glycol derivative of the formula (I) is less than 30% by weight, the storage life of the resulting polyisocyanate is slightly shortened whereas if the amount is more than 90% by weight a precipitate tends to be formed in the reaction mixture. Thus, the amount of the phosphoric acid derivative of the formula (II) is employed in an amount of 70 to 10% by weight, preferably 50 to 30% by weight, with these disadvantages being eliminated.

With respect to the proportions of the diisocyanate monomer and water which are to be reacted with each other, the lower is the ratio of the diisocyanate monomer to the water, the higher is the molecular weight of the resulting polyisocyanate. This is not preferred from the standpoint of the quality of the product. On the other hand, the higher is the ratio of the diisocyanate monomer to the water, the lower is the molecular weight and viscosity of the polyisocyanate, but this is not economical because the amount of the diisocyanate which must be separated and recovered from the reaction system is increased. Therefore, in accordance with the present invention a suitable molar ratio of the diisocyanate monomer to water ranges from about 5:1 to about 40:1.

The preferred reaction temperature for the diisocyanate monomer and water in the process of this invention ranges from about 70° to about 200° C. If the reaction temperature is lower than about 70° C., polyurea is produced and production of the desired polyisocyanate is inhibited, and if the reaction temperature is higher than about 200° C., the resulting polyisocyanate is colored to an undesired extent.

After completion of the reaction, excess diisocyanate monomer and the solvent mixture preferably are recovered from the reaction system as soon as possible and at a temperature as low as possible, since the resulting polyisocyanate further polymerizes or is colored when the reaction system is allowed to stand at a high temperature for a long period of time. Therefore, a film vacuum evaporator, a wiped thin film evaporator, a molecular still and the like are preferably used. In most cases, the distillation equipment described above is operated under a vacuum.

Further, it is preferred for the amount of the residual diisocyanate monomer that is present in the polyisocyanate produced to be minimized, otherwise, due to a high content of the residual diisocyanate monomer the polyisocyanate is not only odorous but is sufficiently toxic as to cause a rash.

Several advantages are obtained by using the solvent mixture of the present invention in the reaction between a diisocyanate monomer and water under the conditions described above. Some of these are set forth below.

Firstly, the polyisocyanate produced by the process of this invention is stabilized, that is, separation of the monomer can be prevented even after the polyisocyanate has been stored for a long period of time. After the stabilized polyisocyanate has been stored at room temperature for one year in a conventional container such as a drum, an 18-liter can, a glass bottle or a plastic bottle, the increase in the monomer content that can be detected by gas chromatography or liquid chromatography is about 0.5% at most, and even with this increased amount plus the residual monomer initially present, the overall content of the monomer is maintained sufficiently low.

Secondly, the formation of polyurea as a precipitate is prevented. This provides many advantages when the process of this invention is performed on an industrial basis. For instance the formation of scale can be prevented, filtration becomes unnecessary and continuous operation for a long period of time becomes possible.

Thirdly, the reaction rate is increased, and this results in a product having excellent qualities free of coloration.

Fourthly, a product having a narrow molecular-weight distribution and low molecular weight is obtained. Such a polyisocyanate having a low molecular weight and a low viscosity is very advantageous for making a high-solid type paint.

Fifthly, if the NCO content per unit weight of polyisocyanate is high, it is very economical for paint manufacturing since a larger quantity of inexpensive polyols per unit weight of polyisocyanate can be used. A polyisocyanate having a low molecular weight and a narrow molecular weight distribution has a higher NCO content than a polyisocyanate having a high molecular weight and broad molecular weight distribution. Therefore, the polyisocyanate product obtained by this invention is economically advantageous from this standpoint as well. In contrast polyisocynates obtained as in the prior art, under reaction conditions where polyurea is formed as a precipitate, inevitably have such a broad molecular-weight distribution that high molecular weight materials are present. This makes it difficult to obtain a product of low viscosity. On the other hand, in accordance with the present invention a product of a narrow molecular-weight distribution can be obtained and this makes it possible to produce a product of low viscosity with a high isocyanate content. In addition to use as a paint, the polyisocyanate produced according to the process of this invention can be employed as a polymer modifier, a fiber processing agent or an adhesive.

The process of this invention is described in greater detail by reference to the following working examples and reference examples. Unless otherwise indicated herein, all parts, percents, ratios and the like are by weight.

EXAMPLE 1

50 g of water was added to a liquid mixture of 6,700 g of hexamethylene diisocyanate, 1,000 g of trimethyl phosphate and 2,300 g of ethylene glycol monomethyl ether acetate under a nitrogen atmosphere at atmospheric pressure in a reaction vessel provided with a reflux condenser, while stirring, and the temperature was increased to 160° C. over a 20 minute period. The reaction was further continued at 160° C. for 60 minutes. No precipitate such as polyurea was formed in the reaction mixture. Thereafter, unreacted hexamethylene diisocyante, trimethyl phosphate and ethylene glycol monomethyl ether acetate was recovered from the reaction mixture at 0.2 mmHg and 180° C. using a thin film evaporator, thereby to obtain as a residue 1,190 g of a polyisocyanate containing 0.15 wt% of unreacted hexamethylene diisocyanate. The thus-obtained polyisocyanate had an NCO content of 23.9 wt%, and a viscosity of 1,200 cP at 30° C. (measured using an Emila Pheometer (rotation viscometer produced by Emila Co., Ltd.), hereinafter the same). The amounts of the hexamethylene diisocyanate present in the polyisocyanate (measured using a Shimazu GC 4CM-PF (produced by Shimazu Seisaksho), gas chromatographic analyzer, hereinafter the same) after storage at 50° C. for 4 weeks and storage at room temperature (15° to 20° C., hereinafter the same) for 1 year were 0.62 wt% and 0.6 wt%, respectively.

EXAMPLE 2

A liquid mixture of 7,000 g of hexamethylene diisocyanate, 500 g of trimethyl phosphate and 2,500 g of diethylene glycol dimethyl ether and 50 g of water were reacted under a nitrogen atmosphere at atmospheric pressure in the same type of reaction vessel as used in Example 1, and the temperature was increased to 150° C. over a 30 minute period, and further the reaction was continued for 90 minutes at 150° C. No precipitate such as polyurea was formed in the reaction mixture. Thereafter, the same type of evaporator as used in Example 1 was used to recover the unreacted hexamethylene diisocyanate and the solvents from the reaction mixture at 0.3 mmHg and 185° C. thereby to obtain as a residue 1,250 g of a polyisocyanate containing 0.2% by weight of unreacted hexamethylene diisocyanate. The NCO content of the thus-obtained polyisocyanate was 23.8 wt% and the viscosity thereof was 1,250 cP at 30° C. The amounts of hexamethylene diisocyanate present in the polyisocyanate after storage at 50° C. for 4 weeks and storage for one year at room temperature were 0.57 wt% and 0.59 wt%, respectively.

EXAMPLE 3

The same reaction and recovery procedures as described in Example 1 were repeated except that 2,300 g of ethylene glycol di-n-butyl ether was used instead of ethylene glycol monomethyl ether acetate. No precipitate such as polyurea was formed in the reaction mixture. Thus, 1,180 g of a polyisocyanate containing 0.18 wt% of unreacted hexamethylene diisocyanate was obtained. The NCO content thereof was 24.0 wt% and the viscosity thereof was 1,150 cP at 30° C. The amount of hexamethylene diisocyanate was 0.6 wt% after the polyisocyanate obtained was stored at room temperature for one year.

EXAMPLE 4

A liquid mixture of 6,200 g of tetramethylene diisocyanate, 600 g of trimethyl phosphate and 1,000 g of ethylene glycol monoethyl ether acetate and 54 g of water were subjected to the same reaction and recovery procedures as described in Example 1. No precipitate such as polyurea was formed in the reaction mixture. The residue was 1,120 g of a polyisocyanate containing 0.1 wt% of tetramethylene diisocyanate and having an NCO content of 28.7 wt%. The viscosity of the residue was 1,000 cP at 30° C. The amounts of the tetramethylene diisocyanate present in the polyisocyanate after storage at 50° C. for 4 weeks and storage at room temperature for one year were 0.6 wt% and 0.6 wt%, respectively.

EXAMPLE 5

A liquid mixture of 7,000 g of xylylene diisocyanate, 1,500 g of trimethyl phosphate and 1,500 g of ethylene glycol diacetate, and 34 g of water were reacted under a nitrogen atmosphere at atmospheric pressure, and the temperature was increased to 130° C. over about a 30 minute period, and further the reaction was continued at 130° C. for 20 minutes. No precipitate such as polyurea was formed in the reaction mixture. A thin film evaporator was used to recover the unreacted xylylene diisocyanate and the solvents from the reaction mixture at 0.5 mmHg and 220° C. The residue was 1,040 g of a polyisocyanate containing 0.3 wt% of unreacted xylylene diisocyanate and having an NCO content of 22.4 wt%. The viscosity of the residue was 3,000 cP at 50° C. The amounts of xylylene diisocyanate present in the polyisocyanate after storage at 50° C. for 4 weeks and storage at room temperature for one year were 0.65 wt% and 0.61 wt%, respectively.

EXAMPLE 6

The same reaction and recovery procedures as described in Example 1 were repeated except that a mixture of trimethyl phosphate and triethyl phosphate (mixing ratio of 1:1 by weight) was used instead of trimethyl phosphate. No precipitate such as polyurea was formed in the reaction mixture. The residue was 1,210 g of a polyisocyanate containing 0.25 wt% of unreacted hexamethylene diisocyanate and having an NCO content of 23.9 wt%. The viscosity of the residue was 1,100 cP at 30° C. The amounts of the hexamethylene diisocyanate present in the polyisocyanate which was stored at 50° C. for 4 weeks and at room temperature for one year were 0.60 wt% and 0.59 wt%, respectively.

EXAMPLE 7

The same reaction and recovery procedures as described in Example 2 were repeated except that diethylene glycol methyl ethyl ether was used instead of diethylene glycol dimethyl ether. No precipitate such as polyurea was formed in the reaction mixture. The residue was 1,190 g of a polyisocyanate containing 0.12 wt% of unreacted hexamethylene diisocyanate, and having an NCO content of 23.9 wt%. The viscosity of the residue was 1,100 cP at 30° C. The amounts of hexamethylene diisocyanate present in the polyisocyanate stored at 50° C. for 4 weeks and at room temperature for one year were 0.67 wt% and 0.65 wt%, respectively.

EXAMPLE 8

The same reaction and recovery procedures as described in Example 1 were repeated except that 96 g of water was used instead of 50 g of water. No precipitate such as polyurea was formed in the reaction mixture. The residue was 2,340 g of a polyisocyanate containing 0.2 wt% of unreacted hexamethylene diisocyanate and having an NCO content of 22.7 wt%. The viscosity of the residue was 3,000 cP at 30° C. The amounts of hexamethylene diisocyanate present in the polyisocyanate stored at 50° C. for 4 weeks and at room temperature for one year were 0.6 wt% and 0.62 wt%, respectively.

EXAMPLE 9

The same reaction and recovery procedures as described in Example 1 were repeated except that triethyl phosphate was used instead of trimethyl phosphate. No precipitate such as polyurea was formed in the reaction mixture. The residue was 1,190 g of a polyisocyanate containing 0.30 wt% of unreacted hexamethylene diisocyanate and having an NCO content of 23.8 wt%. The viscosity of the residue was 1,190 cP at 30° C. The amounts of hexamethylene diisocyanate present in the polyisocynate stored at 50° C. for 4 weeks and at room temperature for one year were 0.64 wt% and 0.65 wt%, respectively.

EXAMPLE 10

A liquid mixture of 5,040 g of hexamethylene diisocyanate, 1,000 g of triethyl phosphate and 1,500 g of diethylene glycol dimethyl ether and 36 g of water was reacted under a nitrogen atmosphere at atmospheric pressure in the same type of reaction vessel as used in Example 1, and the temperature was increased to 150° C. over a 30 minute period, and then the reaction was continued at 150° C. for 90 minutes. No precipitate such as polyurea was formed in the reaction mixture. Thereafter, the same type of evaporator as used in Example 1 was used to recover the unreacted hexamethylene diisocyanate and the solvents at 0.3 mmHg and 185° C. The residue was 890 g of a polyisocyanate containing 0.20 wt% of reacted hexamethylene diisocyanate and having an NCO content of 23.9 wt%. The viscosity of the residue was 1,200 cP at 30° C. The amounts of the hexamethylene diisocyanate present in the polyisocyanate stored at 50° C. for 4 weeks and at room temperature for one year were 0.60 wt% and 0.62 wt%, respectively.

EXAMPLE 11

A liquid mixture of 6,200 g of tetramethylene diisocyanate, 600 g of triethyl phosphate and 1,000 g of ethylene glycol monoethyl ether acetate and 54 g of water was subjected to the same reaction and recovery procedures as described in Example 1. No precipitate such as polyurea was formed in the reaction mixture. The residue was 1,100 g of a polyisocyanate containing 0.24 wt% of unreacted tetramethylene diisocyanate and having an NCO content of 28.5 wt%. The viscosity of the residue was 1,100 cP at 30° C. After the polyisocyanate was stored at room temperature for one year, the amount of the tetramethylene diisocyanate present therein was 0.70 wt%.

EXAMPLE 12

A liquid mixture of 3,330 g of isophorone diisocyanate, 550 g of triethyl phosphate and 1,090 g of ethylene glycol monomethyl ether acetate and 18 g of water was subjected to the same reaction and recovery procedures as described in Example 1. No precipitate such as polyurea was formed in the reaction mixture. The residue was 566.0 g of a polyisocyanate containing 0.3 wt% of isophorone diisocyanate and having an NCO content of 17.7 wt%. The viscosity of the residue was 3,000 cP at 50° C. The amounts of the isophorone diisocyanate present in the polyisocyanate after storage at 50° C. for 4 weeks and storage at room temperature for one year were 0.65 wt% and 0.67 wt%, respectively.

EXAMPLE 13

47.9 g of water was added to a liquid mixture of 6,700 g of hexamethylene diisocyanate, 500 g of trimethyl phosphate, 500 g of tripropyl phosphate and 2,300 g of ethylene glycol monomethyl ether acetate under a nitrogen atmosphere at atmospheric pressure in a reaction vessel provided with a reflux condenser, while stirring, and the temperature was increased to 160° C. over a 20 minute period. The reaction was further continued at 160° C. for 60 minutes. No precipitate such as polyurea was formed in the reaction mixture. Then, a thin film evaporator was used to recover the unreacted hexamethylene diisocyanate, trimethyl phosphate, tripropyl phosphate and ethylene glycol monomethyl ether acetate from the reaction mixture thereby to obtain as a residue 1,130 g of a polyisocyanate containing 0.30 wt% of unreacted hexamethylene diisocyanate and having an NCO content of 24.0 wt%. The viscosity of the residue was 1,180 cP at 30° C. The amounts of hexamethylene diisocyanate contained in the polyisocyanate stored at 50° C. for 4 weeks and at room temperature for one year were 0.65 wt% and 0.66 wt%, respectively.

EXAMPLE 14

36 g of water was added to a liquid mixture of 5,040 g of hexamethylene diisocyanate, 300 g of triethyl phosphate, 700 g of tributyl phosphate and 1,500 g of ethylene glycol dimethyl ether under a nitrogen atmosphere at atmospheric pressure in a reaction vessel provided with a reflux condenser, while stirring, and the temperature was increased to 150° C. over a 30 minute period. The reaction was further continued at 150° C. for 90 minutes. No precipitate such as polyurea was formed in the reaction mixture. Then, a thin film evaporator as described in Example 13 was used to recover the unreacted hexamethylene diisocyanate and the solvent from the reaction mixture thereby to obtain as a residue 880 g of a polyisocyanate containing 0.20 wt% of unreacted hexamethylene diisocyanate and having an NCO content of 23.9 wt%. The viscosity of the residue was 1,180 cP at 30° C. The amounts of the hexamethylene diisocyanate present in the polyisocyanate stored at 50° C. for 4 weeks and at a room temperature for one year were 0.60 wt% and 0.62 wt%, respectively.

EXAMPLE 15

A liquid mixture of 6,720 g of hexamethylene diisocyanate, 600 g of trimethyl phosphate, 600 g of dimethyl ethyl phosphate, 600 g of triethyl phosphate, 888 g of diethyl methyl phosphate and 4,032 g of ethylene glycol monoisopropyl ether acetate and 18.9 g of water was subjected to the same reaction and recovery procedures as described in Example 1. No precipitate such as polyurea was formed in the reaction mixture. The residue was 470 g of a polyisocyanate containing 0.2 wt% of the unreacted hexamethylene diisocyanate and having an NCO content of 24.5 wt%. The viscosity of the residue was 750 cP at 30° C. The amount of hexamethylene diisocyanate present in this polyisocyanate after storage at room temperature for one year was 0.68 wt%.

EXAMPLE 16

A liquid mixture of 3,360 g of hexamethylene diisocyanate, 2,500 g of trimethyl phosphate 2,500 g of tributyl phosphate and 5,080 g of ethylene glycol monomethyl ether acetate and 24 g of water was subjected to the same reaction and recovery procedures as described in Example 1. No precipitate such as polyurea was formed in the reaction mixture. The residue was 571 g of a polyisocyanate containing 0.23 wt% of the unreacted hexamethylene diisocyanate and having an NCO content of 23.8 wt%. The viscosity of the residue was 1,150 cP at 30° C. The amount of hexamethylene diisocyanate present in this polyisocyanate after storage at room temperature for one year was 0.67 wt%.

EXAMPLE 17

A liquid mixture of 6,700 g of hexamethylene diisocyanate, 1,100 g of trimethyl phosphate, 1,000 g of ethylene glycol monomethyl ether acetate and 1,300 g of ethylene glycol monoethyl ether acetate and 48 g of water was subjected to the same reaction and recovery procedures as described in Example 2. No precipitate such as polyurea was formed in the reaction mixture. The residue was 1,100 g of a polyisocyanate containing 0.23 wt% of the unreacted hexamethylene diisocyanate and having an NCO content of 23.8 wt%. The viscosity of the residue was 1,150 cP at 30° C. The amount of hexamethylene diisocyanate present in this polyisocyanate after storage at room temperature for one year was 0.63 wt%.

REFERENCE EXAMPLE 1

To a liquid mixture of 7,000 g of hexamethylene diisocyanate and 2,500 g of trimethyl phosphate in a reaction vessel equipped with a reflux condenser, 50 g of water was added under a nitrogen atmosphere at atmospheric pressure while stirring, the temperature was increased to 160° C. over a 20 minute period, and the reaction was continued at 160° C. for 60 minutes. No precipitate such as polyurea was formed in the reaction mixture. Then, a thin film evaporator was used to recover the unreacted hexamethylene diisocyanate and the solvent from the reaction mixture at 0.2 mmHg and 180° C. The residue was 1,260 g of a polyisocyanate containing 0.3 wt% of unreacted hexamethylene diisocyanate and having an NCO content of 24.2 wt%. The viscosity of the residue was 1,000 cP at 30° C. The amounts of the hexamethylene diisocyanate present in the polyisocyanate stored at 50° C. for 4 weeks and at room temperature for one year were 1.5 wt% and 1.4 wt%, respectively.

REFERENCE EXAMPLE 2

A liquid mixture of 6,720 g of hexamethylene diisocyanate and 1,000 g of triethyl phosphate and 72 g of water was reacted under a nitrogen atmosphere at atmospheric pressure in the same type of reaction vessel as described in Reference Example 1, with the temperature of the mixture being increased to 140° C. over a 30 minute period, and the reaction was further continued for 120 minutes at 140° C. No precipitate such as polyurea was formed in the reaction mixture. The unreacted hexamethylene diisocyanate and the solvent were recovered from the reaction mixture in the same manner as described in Reference Example 1. The residue was 1,800 g of polyisocyanate containing 0.30 wt% of unreacted hexamethylene diisocyanate and having an NCO content of 23.4 wt%. The viscosity of the residue was 1,550 cP at 30° C. After the polyisocyanate was stored at room temperature for one year, the amount of the hexamethylene diisocyanate present therein was 1.40 wt%.

REFERENCE EXAMPLE 3

A liquid mixture of 6,200 g of tetramethylene diisocyanate and 2,100 g of trimethyl phosphate and 54 g of water was subjected to the same reaction and recovery procedures as described in Reference Example 1. No precipitate such as polyurea was formed in the reaction mixture. The residue was 1,125 g of a polyisocyanate containing 0.2 wt% of unreacted tetramethylene diisocyanate and having an NCO content of 29.1 wt%. The viscosity of the residue was 1,100 cP at 30° C. The amounts of the tetramethylene diisocyanate present in the polyisocyanate stored at 50° C. for 4 weeks and at room temperature for one year were 1.5 wt% and 1.4 wt%, respectively.

REFERENCE EXAMPLE 4

The same reaction and recovery procedures as described in Reference Example 1 were repeated except that 2,500 g of ethylene glycol monomethyl ether acetate was used instead of trimethyl phosphate. About 20 g of polyurea precipitated from the reaction mixture. The unreacted hexamethylene diisocyanate and the solvent were recovered in the same manner as described in Reference Example 1. The residue was 1,160 g of a polyisocyanate containing 0.3 wt% of unreacted hexamethylene diisocyanate and having an NCO content of 24.3 wt%. The viscosity of the residue was 820 cP at 30° C. The amounts of the hexamethylene diisocyanate contained in the polyisocyanate stored at 50° C. for 4 weeks and at room temperature for one year were 0.55 wt% and 0.53 wt%, respectively.

REFERENCE EXAMPLE 5

The same reaction and recovery procedures as described in Reference Example 2 were repeated except that 1,000 g of ethylene glycol monoethyl ether acetate was used instead of triethyl phosphate. About 100 g of polyurea precipitated from the reaction mixture. The residue was 1,800 g of a polyisocyanate containing 0.32 wt% of unreacted hexamethylene diisocyanate and having an NCO content of 23.3 wt%. The viscosity of the residue was 1,550 cP at 30° C. After the polyisocyanate was stored at room temperature for one year, the amount of hexamethylene diisocyanate present therein was 0.7 wt%.

REFERENCE EXAMPLE 6

The same reaction and recovery procedures as described in Reference Example 2 were repeated except that a mixture of trimethyl phosphate and triethyl phosphate (mixing ratio: 1:1 by weight) was used instead of triethyl phosphate. No precipitate such as polyurea was formed in the reaction mixture. The residue was 1,760 g of a polyisocyanate containing 0.30 wt% of unreacted hexamethylene diisocyanate and having an NCO content of 23.5 wt%. The viscosity of the residue was 1,480 cP at 30° C. After the polyisocyanate was stored at room temperature for one year, the amount of hexamethylene diisocyanate present therein was 1.30 wt%.

As can be seen from the results obtained in the above Examples and Reference Examples in Reference Examples 1, 2, 3 and 6, the increase in the monomer content of the polyisocyanate after storage was markedly high, and in Reference Examples 4 and 5 undesired by-product, i.e., polyurea, was produced to a great extent, in comparison with the results obtained with the process of this invention.

While the invention has been described in detail and with reference to specific embodiments thereof, it will be apparent to one skilled in the art that various changes and modifications can be made therein without departing from the sprit and scope thereof.

What is claimed is:

1. In a process for the preparation of an organic polyisocyanate which comprises reacting an aliphatic, alicyclic or araliphatic diisocyanate monomer with water, the improvement which comprises conducting the reaction
    (a) at a reaction temperature of at from about 70° C. to about 200° C.;
    (b) in the presence of a solvent mixture comprising a mixture of at least one ethylene glycol derivative of the formula (I):

$$R_1O(CH_2CH_2O)_nR_2 \quad (I)$$

wherein $R_1$ and $R_2$, which may be the same or different, each represents an alkyl group having 1 to 4 carbon atoms, which may be straight chain or branched chain, or an acetyl group and n is an integer of 1 to 2; and at least one phosphoric acid derivative of the formula (II):

$$\begin{matrix} R_3O \\ R_4O{-}P{=}O \\ R_5O \end{matrix} \quad (II)$$

wherein $R_3$, $R_4$ and $R_5$, which may be the same or different, each represents a methyl group or an ethyl group;
    (c) with the proportion of the solvent mixutre in the reaction mixture being 10 to 80 wt%; and
    (d) with the proportion of the ethylene glycol derivative (I) in the solvent mixture being 30 to 90 wt% and the proportion of the phosphoric acid derivative (II) in the solvent mixture being 10 to 70 wt%, wherein the molar ratio of the diisocyanate monomer to water ranges from about 5:1 to about 40:1, said solvent mixture providing the dual effects of substantially completely eliminating the formation of by-product polyurea and inhibiting the amounts of monomer present after long term storage of the reaction product.

2. The process according to claim 1, wherein the diisocyanate monomer is hexamethylene diisocyanate.

3. The process according to claim 1, wherein the diisocyanate monomer is xylylene diisocyanate.

4. The process according to claim 1, wherein the diisocyanate monomer is isophorone diisocyanate.

5. The process according to claim 2, wherein the diisocyanate monomer is tetramethylene diisocyanate.

6. The process according to claim 1, wherein the alkyl group for $R_1$ and $R_2$ in the ethylene glycol derivative represented by the formula (I) has 1 to 2 carbon atoms.

7. The process according to claim 6, wherein the ethylene glycol derivative of the formula (I) is ethylene glycol monoethyl ether acetate.

8. The process according to claim 6, wherein the ethylene glycol derivative of the formula (I) is diethylene glycol dimethyl ether.

9. The process according to claim 6, wherein the ethylene glycol derivative of the formula (I) is ethylene glycol monomethyl ether acetate.

10. The process according to claim 6, wherein the ethylene glycol derivative of the formula (I) is ethylene glycol diacetate.

11. The process according to claim 1, wherein the phosphoric acid derivative of the formula (II) is trimethyl phosphate.

12. The process according to claim 1, wherein the phosphoric acid derivative of the formula (II) is triethyl phosphate.

13. The process according to claim 1, wherein the phosphoric acid derivative of the formula (II) comprises a mixture of trimethyl phosphate and triethyl phosphate.

14. The process according to claim 1, wherein the solvent comprises a mixture of ethylene glycol monomethyl ether acetate and trimethyl phosphate.

15. The process according to claim 3, wherein the solvent comprises a mixture of ethylene glycol monomethyl ether acetate and trimethyl phosphate.

16. The process according to claim 1, wherein the solvent comprises a mixture of ethylene glycol monomethyl ether acetate and triethyl phosphate.

17. The process according to claim 2, wherein the solvent comprises a mixture of ethylene glycol monomethyl ether acetate and triethyl phosphate.

18. The process according to claim 1, wherein the solvent comprises a mixture of ethylene glycol monomethyl ether acetate, trimethyl phosphate and triethyl phosphate.

19. The process according to claim 2, wherein the solvent comprises a mixture of ethylene glycol monomethyl ether acetate, trimethyl phosphate and triethyl phosphate.

20. The process according to claim 1, wherein the amount of the solvent mixture ranges from 20 to 50 wt% of the total weight of the reaction mixture.

21. The process according to claim 1, wherein the solvent mixture contains an ethylene glycol derivative of the formula (I) in an amount of 50 to 70 wt%.

22. The process according to claim 1, wherein the solvent mixture further contains tripropyl phosphate or tributyl phosphate.

* * * * *